United States Patent
Defreitas et al.

(10) Patent No.: US 11,350,891 B2
(45) Date of Patent: Jun. 7, 2022

(54) COMPRESSION ARM DEVICES AND METHODS

(71) Applicant: HOLOGIC, INC., Marlborough, MA (US)

(72) Inventors: Kenneth Defreitas, Marlborough, MA (US); Alan Rego, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/981,350

(22) PCT Filed: May 22, 2019

(86) PCT No.: PCT/US2019/033559
§ 371 (c)(1),
(2) Date: Sep. 16, 2020

(87) PCT Pub. No.: WO2019/226792
PCT Pub. Date: Nov. 28, 2019

(65) Prior Publication Data
US 2021/0038173 A1    Feb. 11, 2021

Related U.S. Application Data (60) Provisional application No. 62/676,522, filed on May 25, 2018.

(51) Int. Cl.
*A61B 6/00* (2006.01)
*A61B 6/04* (2006.01)

(52) U.S. Cl.
CPC .......... *A61B 6/0414* (2013.01); *A61B 6/502* (2013.01); *A61B 6/0435* (2013.01)

(58) Field of Classification Search
CPC ... A61B 6/0407; A61B 6/0414; A61B 6/0421; A61B 6/0435; A61B 6/502
See application file for complete search history.

(56) References Cited

U.S. PATENT DOCUMENTS

| | | | |
|---|---|---|---|
| 4,250,894 A | 2/1981 | Frei et al. | |
| 4,658,409 A | 4/1987 | Summ | |
| 5,713,356 A | 2/1998 | Kruger | |
| 6,049,583 A | 4/2000 | Galkin | |

(Continued)

FOREIGN PATENT DOCUMENTS

| CN | 202665563 | 1/2013 |
|---|---|---|
| CN | 105726049 | 7/2016 |

(Continued)

OTHER PUBLICATIONS

PCT International Preliminary Report on Patentability in International Application PCT/US2019/033559 dated Dec. 10, 2020, 11 pages.

(Continued)

*Primary Examiner* — Don K Wong
(74) *Attorney, Agent, or Firm* — Merchant & Gould P.C.

(57) ABSTRACT

A compression arm device for compressing a breast in an imaging system with a compression paddle. The compression arm device includes a drive for moving the compression paddle towards the breast such that the drive provides a variable resistance during a contact of the compression paddle with the breast.

20 Claims, 8 Drawing Sheets

(56) References Cited

U.S. PATENT DOCUMENTS

| | | | |
|---|---|---|---|
| 6,091,981 | A | 7/2000 | Cundari et al. |
| 6,620,115 | B2 | 9/2003 | Sarvazyan et al. |
| 8,217,357 | B2 | 7/2012 | Stein et al. |
| 8,594,275 | B2 | 11/2013 | Matsuura |
| 8,753,278 | B2 | 6/2014 | Stoll |
| 8,903,039 | B2 | 12/2014 | Masumoto et al. |
| 9,050,009 | B2 | 6/2015 | Den Heeten et al. |
| 2013/0016807 | A1 | 1/2013 | Kallert et al. |
| 2014/0121520 | A1 | 5/2014 | Wang et al. |
| 2014/0321607 | A1 | 10/2014 | Smith et al. |
| 2014/0328458 | A1 | 11/2014 | Erhard et al. |
| 2014/0348291 | A1 | 11/2014 | Lee et al. |
| 2016/0135772 | A1* | 5/2016 | Nam ............ A61B 6/502 378/37 |
| 2016/0166217 | A1 | 6/2016 | Davis et al. |
| 2016/0183889 | A1 | 6/2016 | Matsuura |
| 2016/0206229 | A1 | 7/2016 | Arai et al. |
| 2016/0228008 | A1 | 8/2016 | Lee |
| 2016/0235379 | A1 | 8/2016 | Homann |
| 2017/0086765 | A1 | 3/2017 | Smith et al. |

FOREIGN PATENT DOCUMENTS

| | | |
|---|---|---|
| DE | 103 34 421 A1 | 2/2004 |
| JP | 4874777 | 2/2012 |
| JP | 5174081 | 4/2013 |
| JP | 5424956 | 2/2014 |
| JP | 5634938 | 12/2014 |
| JP | 5634939 | 12/2014 |
| WO | 2016/076528 A1 | 5/2016 |

OTHER PUBLICATIONS

International Search Report and Written Opinion of the International Searching Authority for International Patent Application No. PCT/US2019/033559 dated Jul. 25, 2019, 18 pages.

Branderhorst, W. et al., "Mammographic compression—A need for mechanical standardization", Feb. 2015, European Journal of Radiology 14(2); 1-7.

Kornguth et al., "Impact of Patient-Controlled Compression on the Mammography Experience", Jan. 1993, Radiology 186;99-102.

Mercer et al., "Practitioner compression force varability in mammography: a preliminary study", The British Institute of Radiology, 2013, 1-9.

Poulos, Ann et al., "Breast Compression in Mammography: How Much is Enough?", Australian Radiology (2003) 47, 121-126.

Sullivan, Daniel et al., "Measurement of Force Applied during Mammography", Nov. 1991, Radiology 181; 355-357.

Tanner, "Mammographic Unit Compression Force: Acceptance Test and Quality Control Protocols", Jul. 1992, Radiology 184; 45-48.

Yaffe et al., "Quality Control for Digital Mammography: Part II Recommednations from the ACRIN DMIST Trial", 2006 Medical Physics 33(3); 737-752.

* cited by examiner

COMPRESSION ARM DEVICES AND METHODS

CROSS-REFERENCE TO RELATED APPLICATIONS

This application is a National Stage Application of PCT/US2019/033559, filed May 22, 2019, which claims priority to U.S. Provisional Patent Application No. 62/676,522, filed May 25, 2018, the disclosures of which are hereby incorporated by reference herein in their entireties. To the extent appropriate, a claim of priority is made to each of the above disclosed applications.

BACKGROUND

Compression during breast imaging, such as mammography and tomosynthesis imaging, serves a number of purposes. For example, it may: (1) make the breast thinner in the direction of x-ray flux and thereby reduces patient radiation exposure from the level required to image the thicker parts of a breast that are not compressed; (2) make the breast more uniform in thickness in the direction of x-ray flux and thereby facilitates more uniform exposure at the image plane over the entire breast image; (3) immobilize the breast during the x-ray exposure and thereby reduces image blurring; and (4) bring breast tissues out from the chest wall into the imaging exposure field and thus allows for more tissue imaging. As the breast is being compressed, typically a technician manipulates the breast to position it appropriately and counter the tendency that compression has of pushing breast tissue toward the chest wall and out of the image field.

Standard compression methods for breast imaging use a movable, rigid, radiolucent compression paddle. The breast is placed on a breast support platform that typically is flat, and the paddle then compresses the breast, usually while a technician or other health professional is holding the breast in place. The technician may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

SUMMARY

The technologies described herein include systems for compressing a breast, as well as particular methods for performing compression of a breast. The methods described herein may be performed by systems having various configurations. Several examples of such systems are described.

In one aspect, the technology relates to a compression arm device for compressing a breast in an imaging system with a compression paddle, the compression arm device including: a drive for moving the compression paddle towards the breast, wherein the drive provides a variable resistance during a contact of the compression paddle with the breast. In an example, a motor is operatively coupled to the compression paddle and configured to move the compression paddle upon operation of the motor; and the drive includes at least one knob operatively coupled to the compression paddle and configured to move the compression paddle upon a rotation of the at least one knob, wherein the at least one knob is configured to provide the variable resistance to the rotation of the at least one knob. In another example, the drive includes: a slide rail stage configured to support the compression paddle; a rotatable leadscrew coupling the motor and the slide rail stage; and a clutch coupling the at least one knob and the slide rail stage; wherein the slide rail stage is configured to linearly move along the leadscrew upon rotation driven by the motor, and wherein upon rotation of the at least one knob, the clutch controls a torque applied on the at least one knob based at least on part on a compressive force exerted by the compression paddle on the breast, thereby providing variable resistance to the rotation of the at least one knob. In yet another example, a brake is coupled to the leadscrew, wherein the brake is selectively engageable with the leadscrew to prevent rotation of the leadscrew. In still another example, the slide rail stage further includes a leadscrew nut, wherein the leadscrew nut is selectively lockable to prevent rotation of the leadscrew nut. In an example, the slide rail stage further includes a solenoid actuator disposed between the leadscrew nut and the at least one knob, wherein upon deactivation of the solenoid actuator, rotation of the at least one knob is configured to mechanically rotate the leadscrew nut such that the slide rail stage moves linearly along the leadscrew.

In another example, the slide rail stage further includes at least one gear coupled between the leadscrew nut and the at least one knob. In yet another example, the slide rail stage further includes a position sensor configured to measure a linear position of the slide rail stage. In still another example, the position sensor includes a rack-and-pinion system. In an example, the clutch is a magnetic particle clutch. In another example, the slide rail stage further includes a rotatable shaft coupled to the clutch and a transmission coupled between the rotatable shaft and the at least one knob, wherein the transmission includes a belt and at least one gear, and wherein the at least one gear is configured to increase torque resistance applied to the at least one knob by the clutch.

In yet another example, the leadscrew is substantially orthogonal to the rotatable shaft. In still another example, a strain gauge is configured to measure compressive force exerted by the paddle. In an example, an encoder is coupled to the at least one knob and communicatively coupled to the motor, wherein upon the rotation of the at least one knob, the encoder communicates with the motor to drive rotation of the leadscrew. In another example, a rotational speed of the leadscrew is based at least partially on a rotational speed of the at least one knob. In yet another example, a rotational speed of the leadscrew is based at least partially on a compressive force exerted by the paddle.

In another aspect, the technology relates to an imagining system including: a rotatable x-ray tube assembly; and a rotatable compression arm assembly including: a compression paddle; a receptor housing disposed opposite the compression paddle; and a compression arm device configured to support the compression paddle, the compression arm device including: a motor; a rotatable leadscrew coupled to the motor; and a slide rail stage coupled the leadscrew and configured to linearly move along the leadscrew, the slide rail stage including at least one rotatable knob positioned proximate the compression paddle, wherein the imaging system is selectively operable between a first condition and a second condition, and wherein in the first condition, the motor drives rotation of the leadscrew such that the slide rail stage moves relative to the receptor housing, and in the second condition, the at least one knob mechanically drives the slide rail stage along the leadscrew such that the slide rail stage moves relative to the receptor housing.

In an example, the compression paddle is laterally moveable with respect to the compression arm device. In another example, the first condition has electrical power to the imaging system, and the second condition has at least one of (a) electrical power to the imaging system, and (b) no electrical power to the imaging system.

In another aspect, the technology relates to a method of compressing a breast for an imaging procedure, the method including: compressing the breast to a first condition by rotating a leadscrew with a motor so as to linearly move a paddle towards the breast, wherein the paddle is coupled to a compression device assembly linearly moveable by the rotatable leadscrew; compressing the breast to a second condition by rotating at least one knob of the compression device assembly so as to move the paddle further towards the breast, wherein the at least one knob includes an encoder in communication with the motor to drive rotation of the leadscrew based at least partially on rotation of the at least one knob; and substantially simultaneously with rotating the at least one knob, adjusting a resistance to rotation of the at least one knob based at least partially on a compressive force exerted by the paddle against the breast.

In an example, adjusting the resistance to rotation of the at least one knob further includes controlling torque resistance on the at least one knob. In another example, compressing the breast to a first condition includes rotating the at least one knob. In yet another example, a rotational speed of the at least one knob at least partially controls a rotational speed of the leadscrew and a linear movement speed of the paddle. In still another example, the compressive force exerted by the paddle against the breast at least partially controls a rotational speed of the leadscrew and a linear movement speed of the paddle. In an example, the method further includes selectively engaging a solenoid actuator coupled between the at least one knob and the leadscrew, wherein upon deactivation of the solenoid actuator, rotating the at least one knob mechanically drives linear movement of the compression device assembly along the leadscrew. In another example, the compression device assembly is coupled to the leadscrew with a slide rail stage, and the method further includes determining a thickness of the compresses breast based on a position of the slide rail stage.

DETAILED DESCRIPTION

Figure 1:
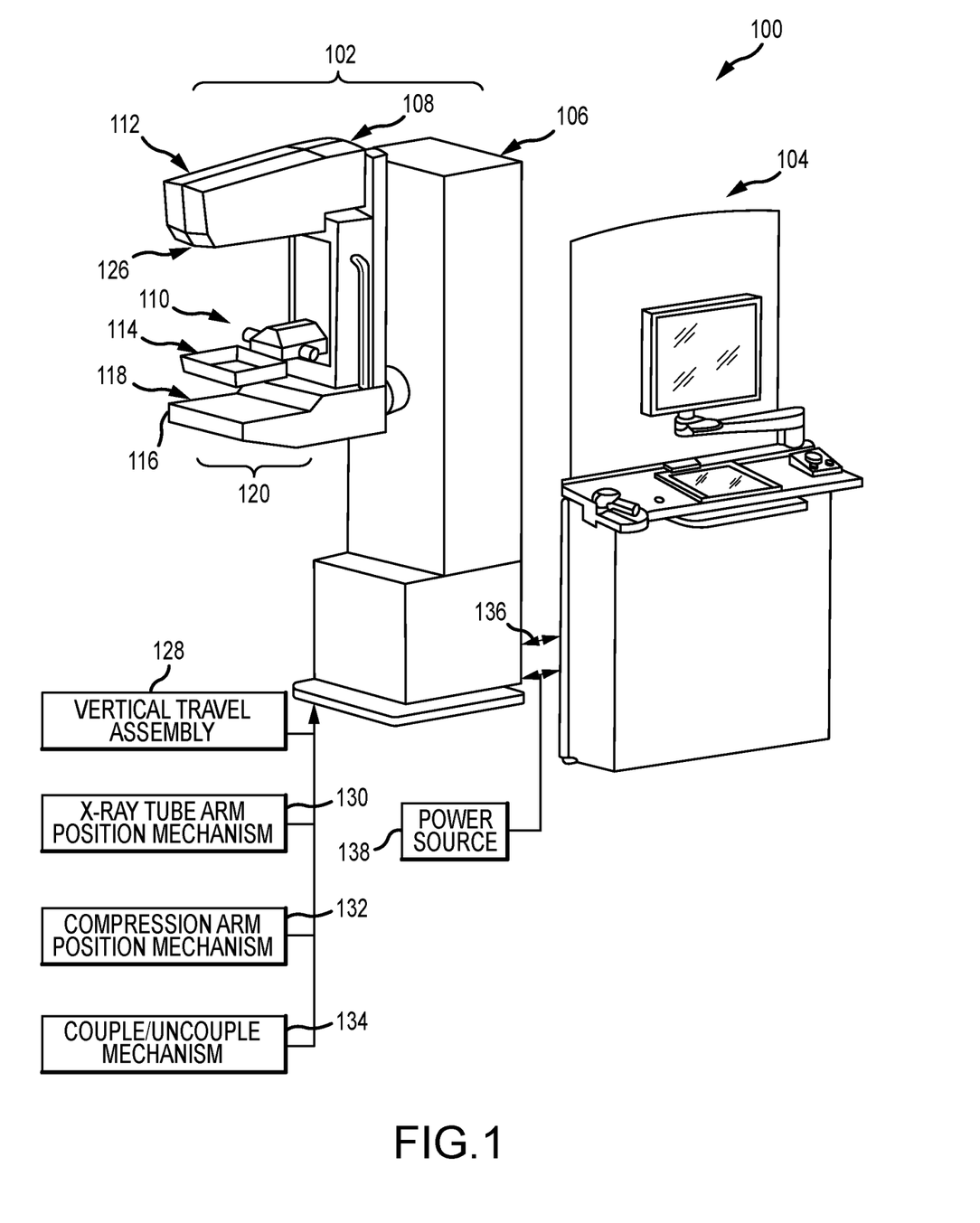
FIG. 1 is a perspective view of an exemplary imaging system.

FIG. 1 is a perspective view of an exemplary imaging system 100. In the example, the imaging system 100 may include a gantry 102 and a data acquisition work-station 104. The gantry 102 includes a housing 106 supporting a tube arm unit 108 that includes a rotatable compression arm assembly 110 and a rotatable x-ray tube assembly 112. The tube arm unit 108 enables a patient's breast to be immobilized for x-ray imagining, such as either, or both, of mammography and tomosynthesis. The compression arm assembly 110 includes a compression paddle 114 and a receptor housing 116 disposed opposite the compression paddle 114. The receptor housing 116 has a compression surface 118 that directly contacts the breast during compression and immobilization. The receptor housing 116 encloses a detector subsystem 120 that includes an image receptor 122 and a retractable anti-scatter grid 124 (both shown in FIGS. 2A and 2B). The compression arm assembly 110 is in a path of an imaging beam that emanates from an x-ray source 126 housed in the x-ray tube assembly 112, such that the beam impinges in the image receptor 122.

The housing 106 may also house and enclose a vertical travel assembly 128 for moving the tube arm assembly 108 up and down to accommodate a particular patient or imaging position. An x-ray tube arm position mechanism 130 to rotate and/or position the x-ray tube assembly 112 for different imaging positions. A compression arm position mechanism 132 to rotate and/or position the compression paddle 114, image receptor 122, and the grid 124. A couple/uncouple mechanism 134 to couple the compression arm assembly 110 and the x-ray tube assembly 112 to and from each other. Generally, the housing 106 includes any suitable motors and electrical and mechanical components and connections to implement these functions as discussed herein. For example, a compression arm device 142 as described below in reference to FIGS. 3-5 may form part of the compression arm position mechanism 132 that controls movement of the compression paddle 114.

The work-station 104 may include a display screen (typically a flat panel display that may include through-screen functionality), user interface devices such as a keyboard, a mouse or trackball, and various switches and indicator lights and/or displays. The work-station 104 also includes computing facilities (e.g., hardware, firmware, and software) for controlling the gantry 102 and for processing, storing, and displaying data and images received from the gantry 102 during imaging operations. The gantry 102 and the work-station 104 may exchange data and controls of a schematically illustrated connection 136. In other examples, the gantry 102 and the work-station 104 may be integration in a single unit. A power source 138 may power the imaging system 100.

Figure 2A:
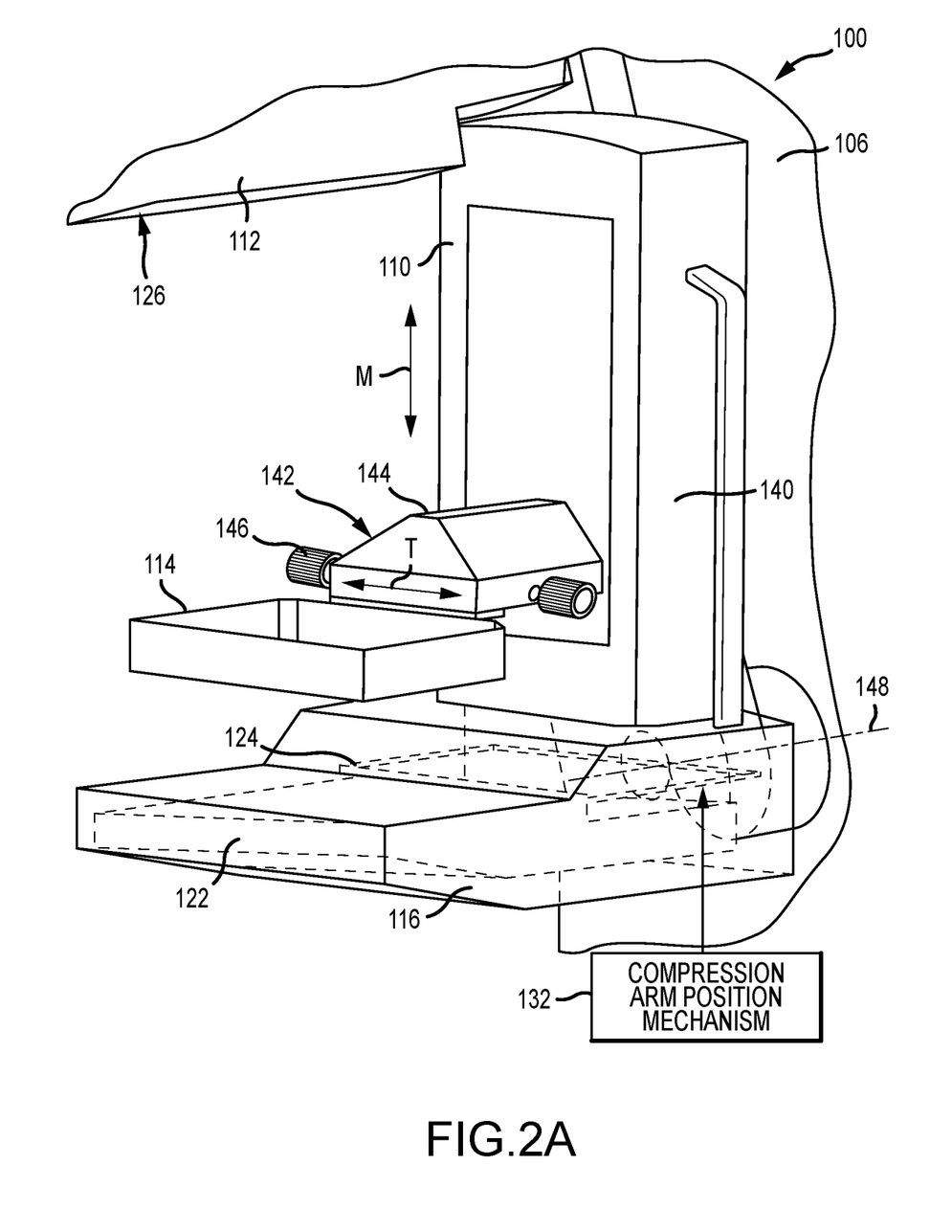
FIG. 2A is a partial enlarged view of the imaging system.
Figure 2B:
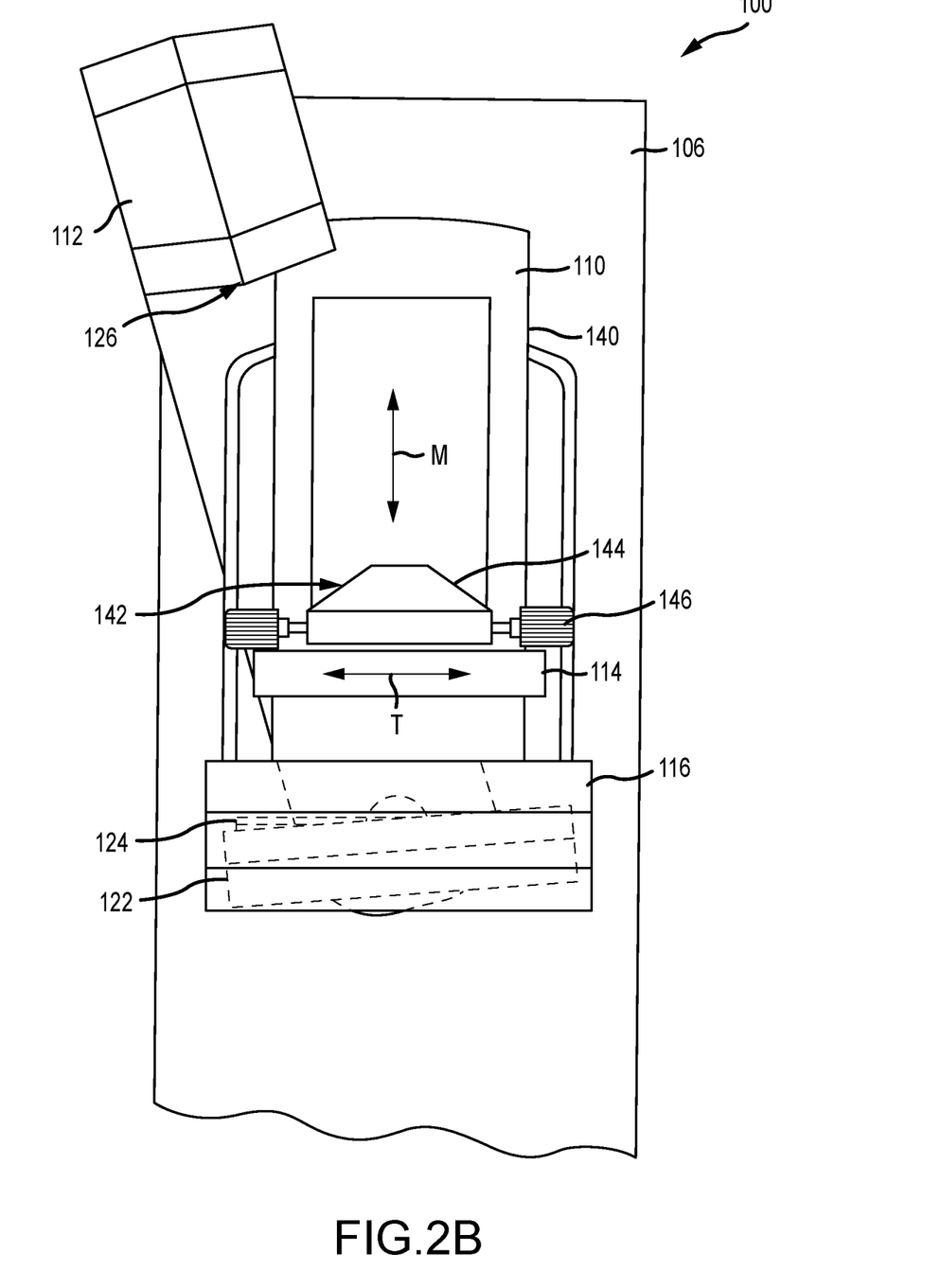
FIG. 2B is a partial front view of the imaging system.

FIG. 2A is a partial enlarged view of the imaging system 100. FIG. 2B is a partial front view of the imaging system 100. Referring concurrently to FIGS. 2A and 2B, certain components are described above, and as such, are not necessary described further. In operation, the imaging system 100 immobilizes a patient's breast for x-ray imaging (either or both of mammography and tomosynthesis) via the compression arm assembly 110 that includes the static receptor housing 116 and the moveable compression paddle 114, both which are coupled to a support arm 140. The compression paddle 114 is configured to move M along the support arm 140 and toward the receptor housing 116 to compress and immobilize the breast. The compression paddle 114 is positionable and supported by a compression arm device 142 that is disposed at least partially within the support arm 140 and at least partially outside of the support arm 140. In some examples, the compression paddle 114 may also be configured to linearly translate T in relation to the compression arm device 142. The compression arm device 142 includes an external compression device assembly 144 that the compression paddle 114 can removably couple thereto. The compression device assembly 144 includes at least one rotatable knob 146, which can be utilized to move the compression paddle 114 as described herein. In the example, the compression arm device 142 may be a component of the compression arm position mechanism 132 (shown in FIG. 2A) that drives motion of the compression paddle 114.

For mammography, the compression arm assembly 110 and the x-ray tube assembly 112 can rotate as a unit about an axis 148 (shown in FIG. 2A) between different imaging orientations such as CC and MLO, so that the imaging system 100 can take a mammogram projection image at each orientation. In mammography imaging operations, the image receptor 122 remains in place relative to the receptor housing 116 while an image is taken. The compression arm assembly 110 can release the breast for movement of one or more of the compression arm assembly 110 and the x-ray tube assembly 112 to a different imaging orientation. For tomosynthesis, the compression arm assembly 110 stays in place, with the breast immobilized and remaining in place, while at least the x-ray tube assembly 112 rotates the x-ray source 126 relative to the compression arm assembly 110 and the compressed breast about the axis 148. The imaging system 100 takes plural tomosynthesis projection images of the breast at respective angles of the x-ray beam relative to the breast.

Concurrently and optionally, the image receptor 122 may be tilted relative to the receptor housing 116 and coordinated with the rotation of the x-ray tube assembly 112. The tilting can be through the same angle as the rotation of the x-ray source 126, but may also be through a different angle selected such that the x-ray beam remains substantially in the same position on the image receptor 122 for each of the plural images. The tilting can be about the axis 148, which can, but need not, be in the image plane of the image receptor 122. The compression arm position mechanism 132 can drive the image receptor 122 in a tilting motion. For tomosynthesis imaging and/or CT imaging, the receptor housing 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging.

When the system is operated, the image receptor 122 produces imaging information in response to illumination by the imaging x-ray beam from the x-ray source 126, and supplies it to an image processor of the work-station 104 (shown in FIG. 1) for processing and generating breast x-ray images. The work-station 104 may control the operation of the imaging system 100 and interacts with the health professional to receive commands and deliver information including processed-ray images.

One challenge with the imaging system 100 is how to immobilize and compress the breast for the desired or required imaging. A health professional, typically an x-ray technician, generally adjusts the breast within the compression arm assembly 110 while pulling tissue towards imaging area and moving the compression paddle 114 toward the receptor housing 116 to immobilize the breast and keep it in place, with as much of the breast tissue as practicable being between the compression paddle 114 and receptor housing 116.

The present technology relates to an electro-mechanical compression arm device as described below for use in a breast imaging system. During imaging of a breast, it is often desirable to immobilize the breast through compression. For instance, by compressing the breast, the breast can be made thinner, thus requiring a lower dose of radiation. Further, by immobilizing the breast, image blurring from movement of the breast during imaging is reduced. Other benefits may also be realized by compressing the breast.

The breast compression procedure, however, may cause discomfort to the patient whose breast is being compressed. One reason for discomfort that the patient may feel is an over-compression of the breast. That is, the mechanisms that drive movement of the compression paddle may not provide feedback, particularly tactile feedback, to the technician as to the amount of compression force being applied to the breast. As such, the technician may unknowingly apply more compression force than needed for the imaging procedure. Furthermore, the mechanisms that drive movement of the compression paddle also require a back-up mechanical drive so that the compressed breast may be released if electrical power goes out during the imaging procedure.

To improve these and other issues, the compression systems described herein include an electro-mechanical compression arm device that provides variable resistance feedback to the technician during the breast compression procedure. In an example, the technician may drive movement of the compression paddle by a rotatable knob through encoder feedback. The knob is coupled to a clutch that provides torque resistance on the knob and provide tactile feedback to the technician based at least partially on a measured compression force on the breast. This system enables the technician to feel (e.g., similar to a pure manual mechanical tightening of a screw) how much compression force is being applied to the breast during the compression procedure through torque resistance on the knob. This feedback reduces over-compression of the breast and increases patient comfort.

Additionally, the knob may be coupled to a mechanical drive system via a solenoid actuator. For example, the knob can be selectively coupled to a leadscrew nut by a transmission, a rotatable shaft, and at least one gear. As such, if the imaging system loses electrical power, the knob automatically engages with the nut on a leadscrew and the technician can move the compression paddle manually, thereby being able to release the compressed breast. In some examples, the mechanical drive system may also be selectively engaged by the solenoid actuator with the electrical power still operable so as to provide the technician more procedure options to compress the patient's breast. For example, the solenoid actuator may engage such that the knob is coupled to the leadscrew nut and enable the technician to facilitate the compression procedure with mechanical resistance feedback to further increase patient comfort during imaging procedures.

Figure 3:
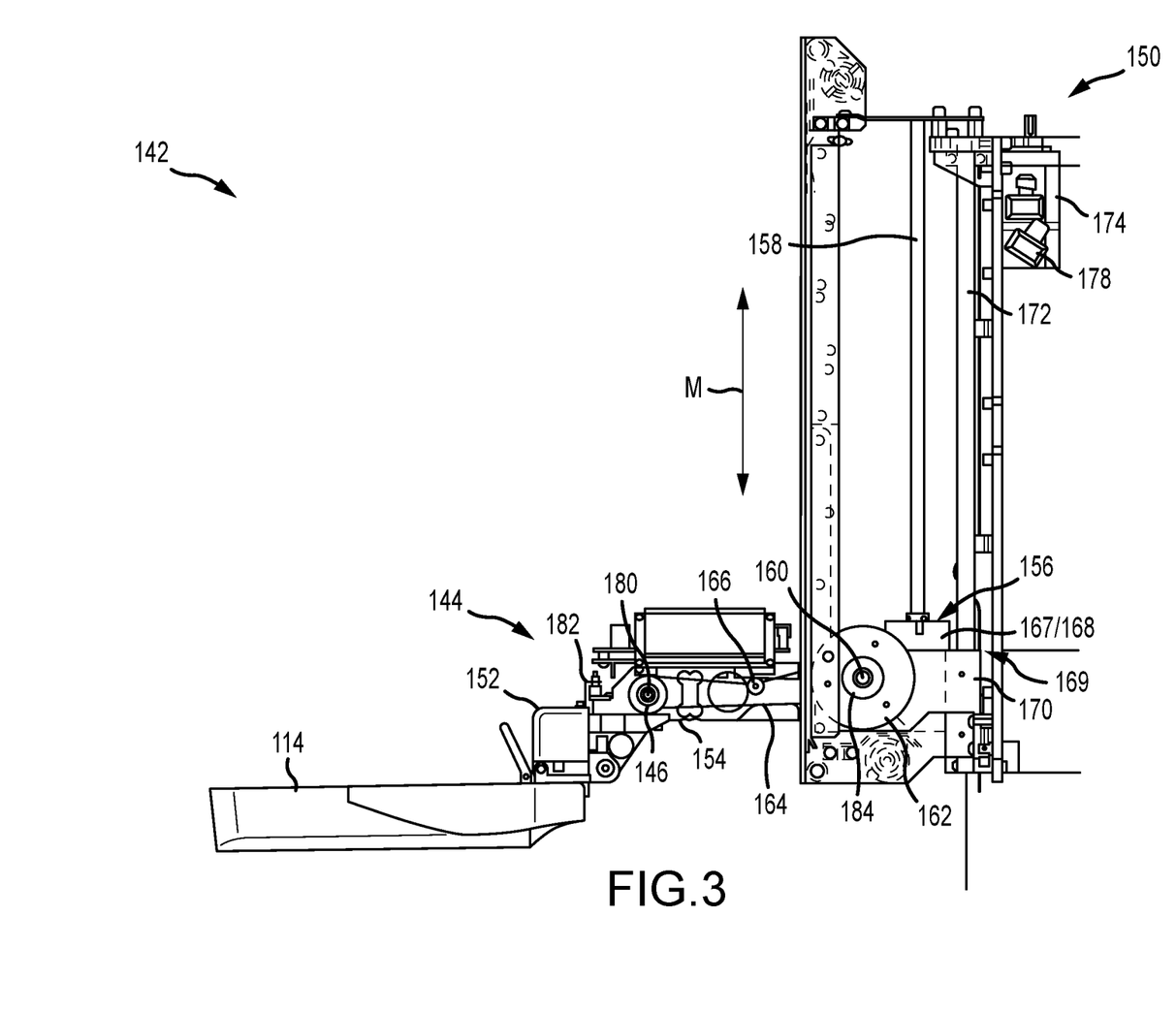
FIG. 3 is a side view of an exemplary compression arm device for use with the imaging system shown in FIGS. 1-2B.

FIG. 3 is a side view of the exemplary compression arm device 142 for use with the imaging system 100 (shown in FIGS. 1-2B). In the example, the compression arm device 142 includes a drive assembly 150 configured to be disposed within the support arm 140 (shown in FIGS. 2A and 2B) and the compression device assembly 144, which extends from the support arm and supports the compression paddle 114. The compression device assembly 144 includes a bracket 152 configured to releasably secure the compression paddle 114. The bracket 152 is mounted on a frame 154 that is configured to securely couple to the drive assembly 150 for movement M. The compression device assembly 144 also include two rotatable knobs 146 (e.g., one on either side of the frame 154) that are configured to drive the movement M of the compression paddle 114, via the compression device assembly 144. The compression device assembly 144 is described further below in reference to FIG. 5.

The drive assembly 150 includes a slide rail stage 156 that supports the compression device assembly 144 and is configured for linear movement M along a rotatable leadscrew 158. The slide rail stage 156 includes a rotatable shaft 160 with a clutch 162 coupled thereto. The clutch 162 is configured to selectively control torque on the shaft 160. In the example, the clutch 162 is a magnetic particle clutch. In other examples, the clutch may be a frictional clutch, a geared clutch, a hydraulic brake, or any other system that enables the slide rail stage to function as described herein. The shaft 160 is coupled to the knob 146 via a transmission 164, such as a pulley belt, chains, or cable. The transmission 164 enables the torque induced on the shaft 160 by the clutch 162, to be transferred to the knob 146 as a resistance force. This torque resistance facilitates providing variable feedback resistance to the technician during the breast compression procedure. As such, the technician may receive tactile feedback on the knob 146 that corresponds to the amount of compression force exerted on the patient's breast (e.g., more torque resistance upon larger compression forces such that the knob is harder to turn and less torque resistance upon smaller compression forces such that the knob is easier to turn). The transmission 164 may include one or more reduction gears 166 that are configured to increase the torque resistance applied to the knob 146 by the clutch 162.

Additionally or alternatively, other types of indicia feedback can be provided to the technician to indicate the extent and/or degree of compression on the patient's breast. For example, audio and/or visual indicia may be used during the breast compression procedure. The audio feedback (e.g., via one or more speakers) may be located on the compression arm device 142 and provide audio cues, for example, a series of cues or a decibel cue level, for the technician. The audio feedback can also be positioned on the work-station. The visual feedback (e.g., via one or more LED diodes or a technician screen) may be located on the compression arm device 142 and provide visual cues, for example, a series of cues or a color cue level, for the technician. The audio feedback can also be positioned on the work-station. The indicia feedback can be changed based upon one or more predetermined factors. For example, indicia can be changed based on exceeding a threshold for force or other known compression factors, and can, optionally, further continue to change based upon increased torque. In one example, visual feedback may be a green-yellow-red color-coded cue.

The slide rail stage 156 also includes a leadscrew nut 168 that is threaded on the leadscrew 158 to enable movement M along the leadscrew 158 as described herein. A nut brake 167 may be coupled to the leadscrew nut 168 to selectively lock rotation of the leadscrew nut 168. In one example, the nut brake 167 may include a pin actuator that engages with the leadscrew nut 168 to prevent rotation thereof. In other examples, any other brake type may be used to facilitate operation of the slide rail stage as described herein. A linear slide 169 is disposed adjacent to the leadscrew 158 to provide resistance to the overturning moment applied by the weight of the compression device assembly 144 and/or the compression force induced by the compression paddle 114. In this example, the linear slide 169 includes a collar 170 that extends opposite of the compression device assembly 144 and is slidingly coupled to a support rod 172. The collar 170 is configured to slide along the rod 172 during movement M of the slide rail stage 156 with little to no resistance (e.g., using a bushing between the collar 170 and the rod 172). The slide rail stage 156 is described further below in reference to FIG. 4B.

Figure 4A:
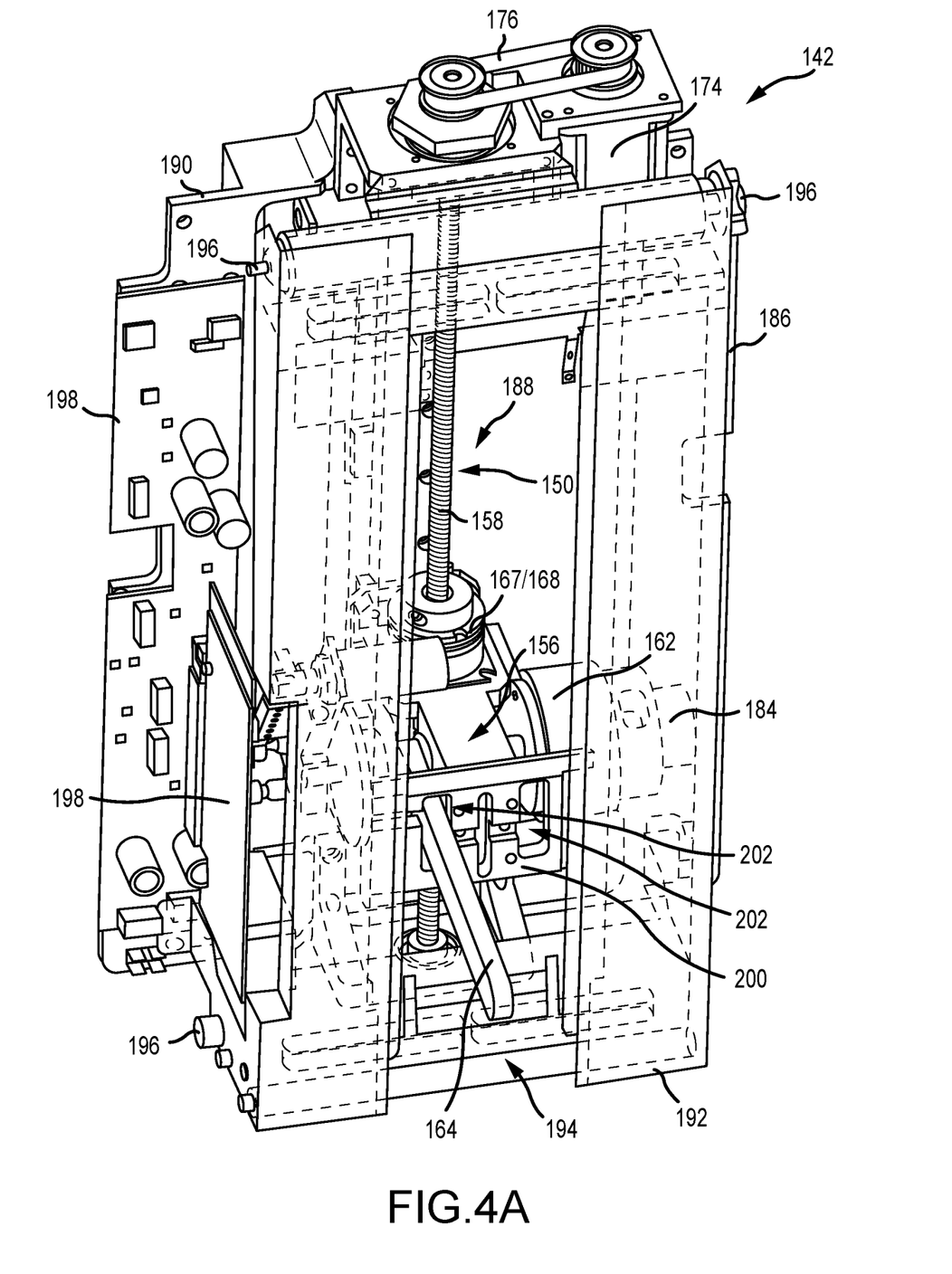
FIG. 4A is a partial perspective view of the compression arm device.
Figure 4B:
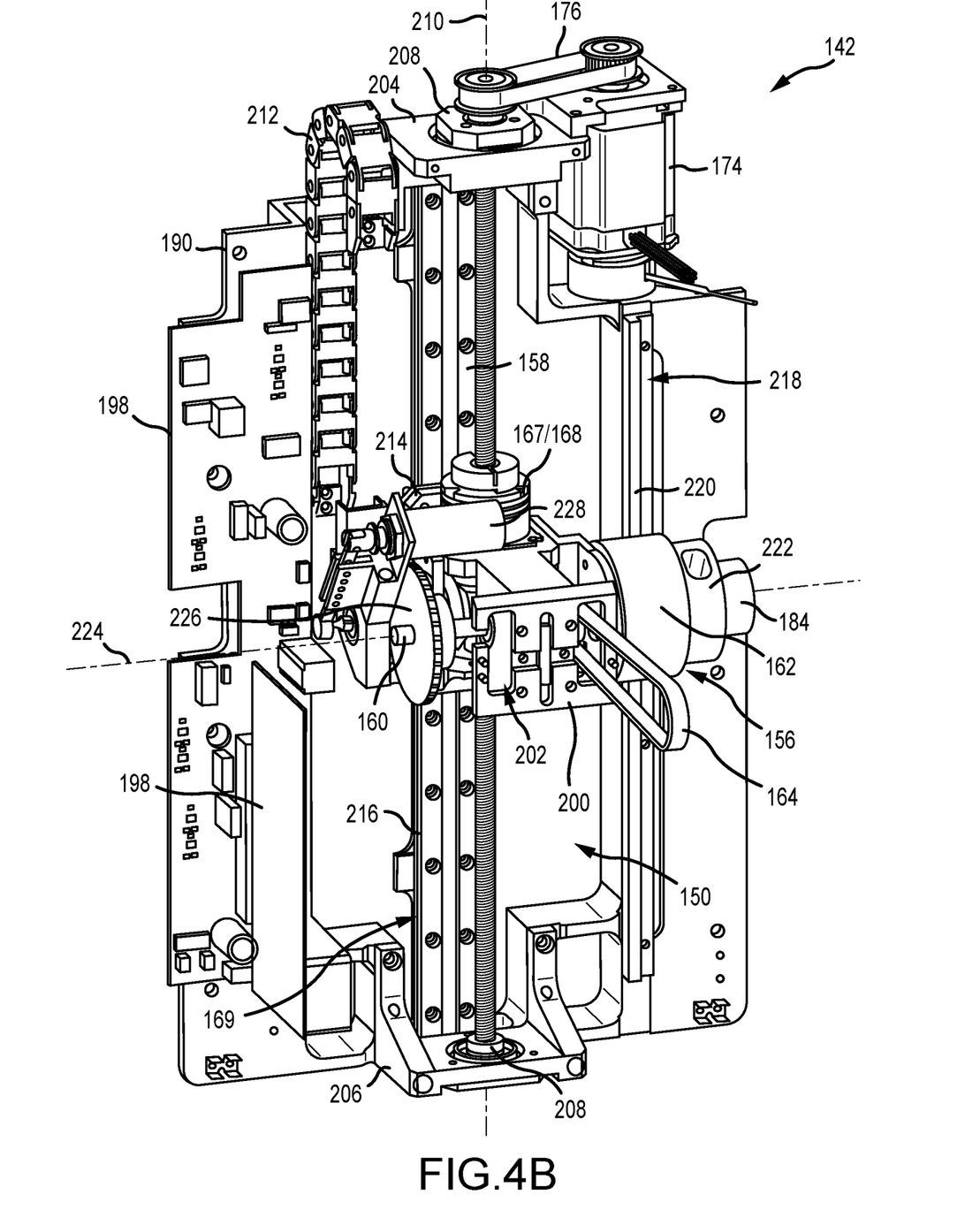
FIG. 4B is an internal partial perspective view of the compression arm device.

The leadscrew 158 is coupled to a motor 174 by a belt drive 176 (shown in FIGS. 4A and 4B). In operation, the compression arm device 142 is operable between two conditions. A first operating condition, where the motor 174 drives rotation of the leadscrew 158, which in turn, moves M the slide rail stage 156 by a locked leadscrew nut 168, and a second operating condition, where the actuation of the knob 146 drives rotation of the leadscrew nut 168, which in turn, moves M the slide rail stage 156. Accordingly, the compression arm device 142 can be driven under electromechanical operation as in the first operating condition (e.g., communication through the motor 174), and can be driven under a pure mechanical operation as in the second operating condition such that the compression arm device 142 maintains operability when electric power is lost. The first operating condition is described below, while the second operating condition is described with reference to FIG. 4B further below. In some examples, in the first operation condition, the actuation of the compression arm device 142 (e.g., via the knobs 146) does not correspond in a one-to-one fashion to the extent of immobilization because the motor is used, and in the second operation condition, the actuation of the compression arm device 142 (e.g., via the knobs 146) does correspond in a one-to-one fashion to the extent of immobilization because a mechanical linkage is used.

To control the motor 174 in the first operating condition, the motor 174 includes one or more encoders 178. In an example, the encoder 178 may provide velocity and position feedback control of the motor 174. As such, the motor 174 can drive rotation of the leadscrew 158 and, thereby, linear position and velocity of the slide rail stage 156, because the leadscrew nut 168 is prevented from rotating by the nut brake 167. In the first operating condition the nut brake 167 is actively engaged to prevent rotation of the leadscrew nut 168. The encoder 178 may be in communication with the work-station 104 (shown in FIG. 1) so that the motor 174 may be remotely controlled for the breast compression procedure. In one example, the work-station may include a foot pedal for the technician to remotely control the position and speed of the compression paddle 114.

The motor 174 may also be communicatively coupled to the knob 146 on the compression device assembly 144, such that rotation of the knob 146 by the technician can also remotely control the motor 174 and, thereby, linear position and velocity of the slide rail stage 156. The knob 146 can include one or more encoders 180 that are in communication with the motor 174 so that upon rotation of the knob 146, the motor 174 drives a corresponding rotation of the leadscrew 158. In an example, the encoder 180 may provide velocity and position feedback of the knob 146. As such, a single primary drive configuration (e.g., the motor and the leadscrew) may be used by one or more components (e.g., the knob and the foot pedal) to control the velocity and position of the compression paddle 114 during breast compression procedures.

Typically, use of the knob 146 by the technician occurs during the final stages of the compression procedure so that the compression profile of the breast is more closely controllable. However, if the knob 146 merely remotely drives the motor 174 by electronic signals, then over-compression of the breast may more easily occur because it is difficult for the technician to know how much compression force the compression paddle 114 is exerting on the patient's breast. As such, in the example, the knob 146 is also coupled to the clutch 162, via the shaft 160 and the transmission 164, such that based on the compressive force exerted by the compression paddle 114 on the patient's breast, variable resistance is induced to the rotation of the knob 146. This variable resistance provides tactile feedback to the technician so that the technician is able to feel, by torque resistance on the knob 146, how much compression force the compression paddle 114 is exerting on the patient's breast, thereby reducing over-compression of the patient's breast.

The compression device assembly 144 includes one or more sensors 182 that are configured to measure the compression force exerted by the compression paddle 114. In one example, the sensor 182 may be a strain gauge positioned between the bracket 152 and the frame 154. The sensor 182 is communicatively coupled to the clutch 162 such that based upon the compressive force exerted by the compression paddle 114, the clutch 162 adjusts the torque resistance induced on the knob 146. As such, the torque resistance on the knob 146 can be proportional to the compression force exerted by the compression paddle 114. The clutch 162 can include one or more encoders 184 that are in communication with the sensor 182. In an example, the encoder 184 may provide resistance feedback control of the clutch 162. As such, the clutch 162 induces torque resistance to the shaft 160, which in turn, is transferred to the knob 146 by the transmission 164. As described above, in some examples, the transmission 164 may be configured to amplify the torque applied to the knob 146.

In some examples, a rotational speed of the knob 146 may be used to at least partially determine the rotational speed of the leadscrew 158, and thus, the velocity of the compression paddle 114. Additionally or alternatively, the compression force exerted by the compression paddle 114 may be used to at least partially determine the rotational speed of the leadscrew 158 so as to reduce over-compression of the patient's breast. Accordingly, the linear velocity of the slide rail stage 156 can be proportional to the rotational speed of the knob 146 and/or the compression force exerted by the compression paddle 114.

FIG. 4A is a partial perspective view of the compression arm device 142. Certain components are described above, and as such, are not necessary described further. The compression arm device 142 includes a housing 186 defining an interior cavity 188 in which the drive assembly 150 including the slide rail stage 156 is disposed. The compression device assembly 144 (shown in FIG. 3) is not illustrated for clarity. The housing 186 may include a back member 190 that supports the components of the compression arm device 142 as described herein. For example, the motor 174 may couple to the back member 190 that provides supporting structure. The housing 186 may also include a front member 192 that defines a front slot 194. The front slot 194 enables the compression device assembly 144 to be coupled to the slide rail stage 156 and extend outward from the housing 186.

The housing 186 may include one or more exterior connection elements 196 that enable the compression arm device 142 to be secured within the support arm 140 of the compression arm assembly 110 (shown in FIGS. 2A and 2B). In the example, the housing 186 is sized and shaped to fit within the above described imaging systems and may also be used as a replacement assembly for use with legacy imaging systems. The housing 186 may also support one or more circuit boards 198 that enable control and operation of the compression arm device 142 as described herein. For example, communication between the compression arm device 142 and the work-station 104 (shown in FIG. 1) and/or communication between encoders and sensors as described in reference to FIG. 3.

The slide rail stage 156 may further include a mounting bracket 200 that is positioned proximate the front slot 194 and that is configured to couple to the frame 154 of the compression device assembly 144 (shown in FIG. 3). The mounting bracket 200 may include two openings 202, each configured to enable the transmission 164 to extend therethrough. In some examples, each knob 146 (shown in FIG. 2A) may be independently rotatable, and as such, each knob is coupled to a transmission system. In other examples, each knob is connected to a single rotatable shaft 230 (shown in FIG. 5), and as such, a single transmission system 164 may be used.

FIG. 4B is an internal partial perspective view of the compression arm device 142. Certain components are described above, and as such, are not necessary described further, and the compression device assembly 144 (shown in FIG. 3) is not illustrated for clarity. In the example, the leadscrew 158 extends between an upper bracket mount 204 and a lower bracket mount 206. The leadscrew 158 is rotatably coupled to each bracket mount 204, 206 by a bearing 208 that enables rotation of the leadscrew 158 about a rotational axis 210. Each bracket mount 204, 206 is coupled to the back member 190 of the housing for a supporting structure. Additionally, a cable housing 212 may be coupled to the back member 190 to enable electronic communication cables to run from the circuit board 198 to the slide rail stage 156 without interfering with the movement of the slide rail stage or any other component within the housing.

The linear slide 169 is disposed adjacent to the leadscrew 158 to provide resistance to the overturning moment applied by the weight of the compression device assembly 144 and/or the compression force induced by the compression paddle 114 (shown in FIG. 3). In this example, however, the linear slide 169 includes a slide 214 that extends from the slide rail stage 156 and is slidingly coupled to a rail 216 that is supported by the back member 190. The slide 214 is configured to slide along the rail 216 during movement of the slide rail stage 156 with little to no resistance. The compression arm device 142 also includes a position sensor 218 that is configured to measure a linear position of the slide rail stage 156. In the example, the position sensor 218 is an analog rack-and-pinion system with a rack 220 disposed on the back member 190 and a pinion 222 extending from the slide rail stage 156. The position sensor 218 enables the imaging system to determine the position of the compression paddle in relation to the receptor housing and calculate a thickness of the compressed breast. In other examples, any other position sensor may be used as required or desired.

The slide rail stage 156 includes a shaft 160 that is rotatable about a rotational axis 224 and coupled to the clutch 162. The clutch 162 is coupled to the knob 146 (shown in FIG. 3) through the transmission 164. The slide rail stage 156 also includes one or more right-angled helical gears 226 coupled to the shaft 160 and a solenoid driven spline shaft actuator 228 that is coupled between the gears 226 and the leadscrew nut 168. In the example, the leadscrew nut 168 is coupled to the nut brake 167 to selectively lock rotation of the leadscrew nut 168 as described above. The solenoid actuator 228 may be configured to selectively engage with the leadscrew nut 168 such that rotation of the shaft 160 may be transferred to the leadscrew nut 168.

As described above, in the first operating condition the motor 174 drives rotation of the leadscrew 158, which in turn, moves the slide rail stage 156 because the leadscrew nut 168 is locked position via the nut brake 167 to prevent rotation thereof. However, this operating condition requires the system to have electric power, because if power to the system is lost, then the motor cannot function. As such, the compression arm device 142 also includes a back-up mechanical system, which does not require electric power so that a patient may be manually released from the imagining system if power is lost. This is the second operating condition, where a mechanical linkage is formed between the knob 146 (shown in FIG. 2A) and the leadscrew nut 168 such that actuation of the knob drives rotation of the leadscrew nut 168, which in turn, moves the slide rail stage 156 along the leadscrew 158.

To control the slide rail stage 156 in the second operating condition, the leadscrew 158 is fixed in place so that rotation about rotation axis 212 is prevented. In one example, to fix the leadscrew 158 a brake may be engaged with the leadscrew 158 to prevent rotation of the leadscrew 158. In the example, the motor 174 may form the brake such that the motor 174 fixes the leadscrew 158 when not in operation. The motor 174 may also fix the position of the leadscrew 158 when power is lost to the imaging system such that the slide rail stage 156 remains stationary and the leadscrew 158 is not back drivable. Other braking devices may also be used as required or desired and that enable the compression arm device to function as described herein.

Additionally, in the second operating condition, the nut brake 167 of the leadscrew nut 168 is released such that the leadscrew nut 168 is free to rotate about the leadscrew rotational axis 210. In one example, upon loss of power the nut brake 167 may automatically release the leadscrew nut 168 from the locked position. However, the leadscrew nut 168 maintains its coupling to the slide rail stage 156. Furthermore, the solenoid actuator 228 deactivates to couple the gears 226 to the leadscrew nut 168. This connection enables for the leadscrew nut 168 to be mechanically rotated and move the slide rail stage 156 along the fixed leadscrew. In one example, upon loss of power, the solenoid actuator 228 automatically deactivates.

In the example, the mechanical linkage may include the following components: the knob, the transmission 164, the shaft 160, the gears 226, the solenoid actuator 228, and the leadscrew nut 168. Accordingly, when the mechanical linkage is engaged in the second operating condition, rotation of the knob drives the transmission 164 to rotate the shaft 160. As the shaft 160 rotates, the gears 226 that are coupled to the leadscrew nut 168 via the solenoid actuator 228 are rotated, which induces rotation of the leadscrew nut 168 to move the slide rail stage 156 along the stationary leadscrew 158. In one example, one rotation of the knob may correspond to approximately 0.3 inches of linear travel along the leadscrew 158. In this example, the rotational axis 210 of the leadscrew 158 is substantially orthogonal to the rotational axis 224 of the shaft 160.

The compression arm device 142 may be automatically switched to the second operating condition when power is lost to the imaging system. When power is lost, the brake on the leadscrew 158 is automatically engaged to prevent rotation of the leadscrew 158, the nut brake 167 on the leadscrew nut 168 is automatically released to enable rotation of the leadscrew nut 168, and the solenoid actuator 228 is automatically deactivated to couple the gears 226 to the leadscrew nut 168. In the example, all of these actions may occur substantially simultaneously. Further, since the clutch 162 is electronic, upon loss of power the clutch 162 is automatically disabled. In other examples, the compression arm device 142 may selectively electronically engage the mechanical linkage when the system has power. This enables for the compression arm device 142 to switch between operating modes (e.g., motor/leadscrew and mechanical linkage) as required or desired. When the mechanical linkage is electronically engaged, the brake on the leadscrew 158 is selectively engaged to prevent rotation of the leadscrew 158, the nut brake 167 on the leadscrew nut 168 is selectively released to enable rotation of the leadscrew nut 168, and the solenoid actuator 228 is selectively deactivated to couple the gears 226 to the leadscrew nut 168, through the system controls. In the example, all of these automatic actions may occur substantially simultaneously.

Figure 5:
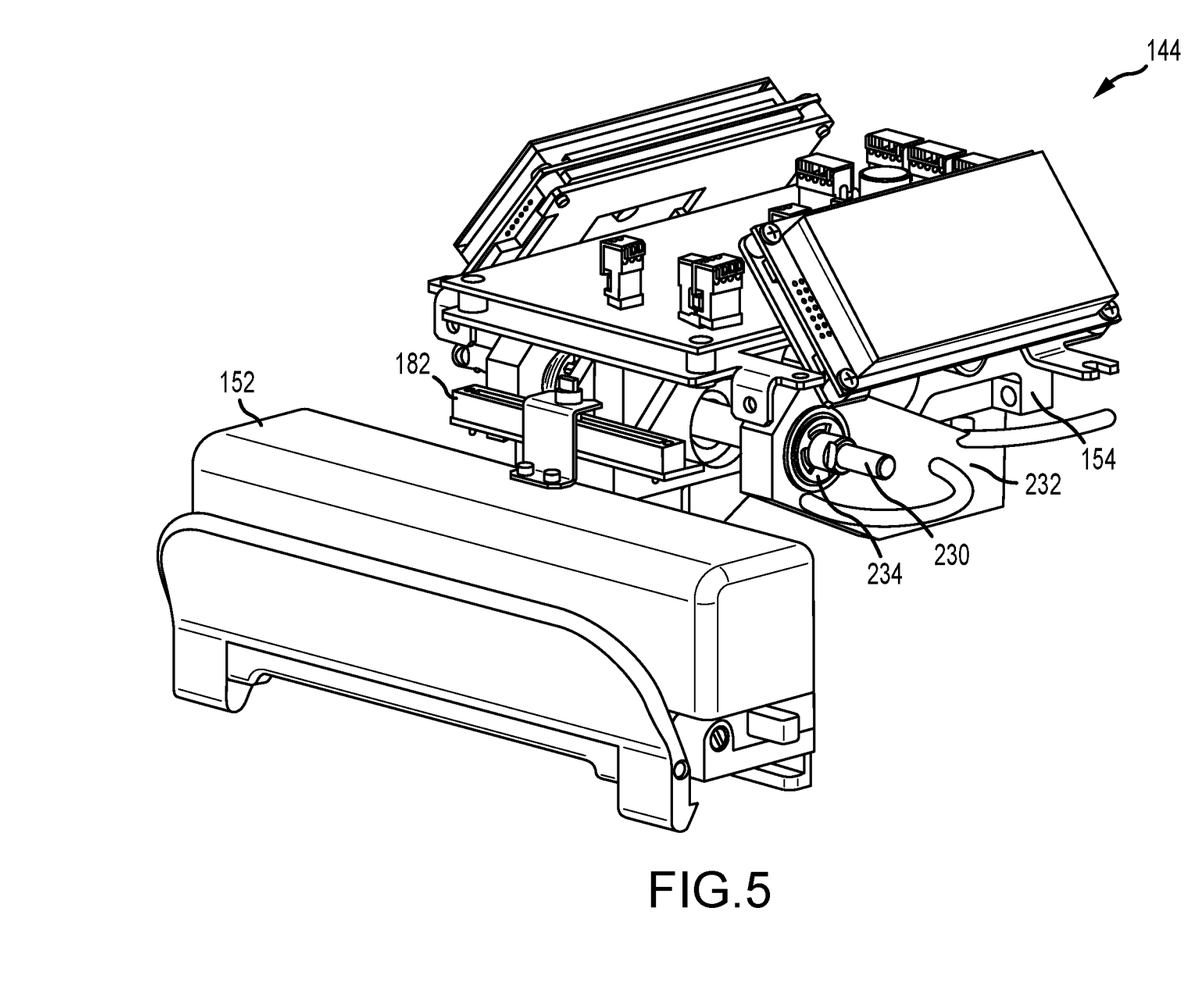
FIG. 5 is a perspective view of an exemplary compression device assembly for use with the compression arm device shown in FIGS. 4A and 4B.

FIG. 5 is a perspective view of the exemplary compression device assembly 144 for use with the compression arm device 142 (shown in FIGS. 4A and 4B). As described above in reference to FIG. 3, the compression device assembly 144 may include the bracket 152 to releasably secure a compression paddle (not shown) to the imaging system. The frame 154 that enables the compression device assembly to be coupled to the drive assembly 150 (shown in FIGS. 4A and 4B), and one or more sensors 182 are positioned between the bracket 152 and the frame 154 to measure the compression force exerted by the compression paddle. The knobs 146 (shown in FIG. 3) are not illustrated for clarity, but are coupled to a rotatable shaft 230. The shaft 230 may couple to the transmission 164 (shown in FIG. 3) so that torque resistance and/or the mechanical linkage extends to the knobs.

The compression device assembly 144 may also include a support structure 232. The shaft 230 extends through and is supported by the support structure 232 by a pair of bearings 234. In the example, the support structure 232 is substantially isolated from sensor 182 such that rotation of the knobs are substantially unreadably by the sensor 182. This is to ensure that any force applied on the knobs (e.g., by the technician) is not used as feedback during the breast compression procedure.

Figure 6:
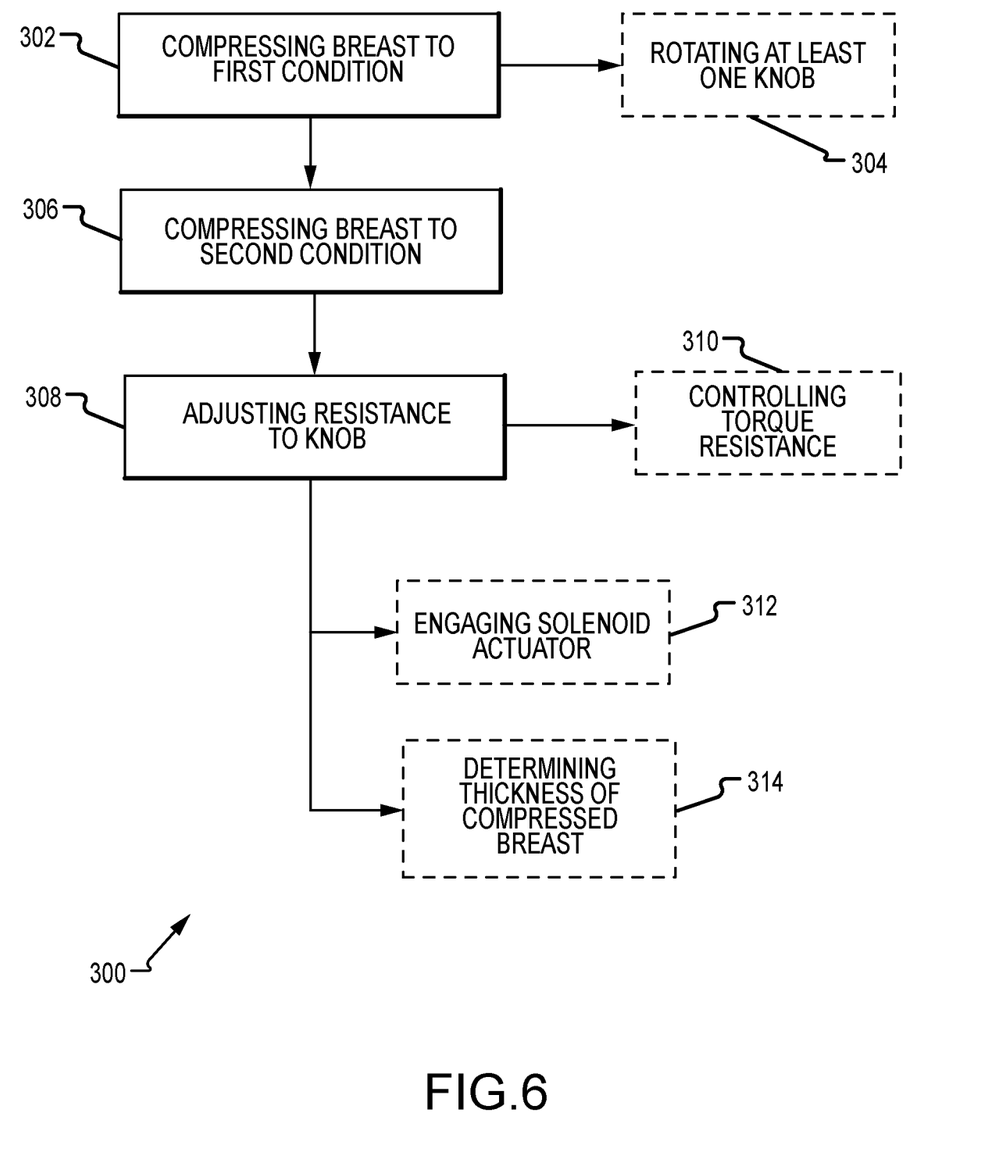
FIG. 6 is a flowchart depicting a method of compressing a breast for an imaging procedure.

FIG. 6 is a flowchart depicting a method 300 of compressing a breast for an imaging procedure. The method 300 begins with compressing the breast to a first condition by rotating a leadscrew with a motor so as to linearly move a paddle towards the breast (operation 302). The paddle may be coupled to a compression device assembly linearly moveable by the rotatable leadscrew. In some examples, at least one knob may be rotated to compress the breast to the first condition (operation 304). In other examples, a remote component, such as a foot pedal or the work-station, may be used. The breast is then compressed to a second condition by rotating at least one knob of the compression device assembly so as to move the paddle further towards the breast (operation 306). The at least one knob includes an encoder in communication with the motor to drive rotation of the leadscrew based at least partially on rotation of the at least one knob. In some examples, a rotational speed of the at least one knob at least partially controls a rotational speed of the leadscrew and a linear movement speed of the paddle. In other examples, the compressive force exerted by the paddle against the breast at least partially controls a rotational speed of the leadscrew and a linear movement speed of the paddle.

Substantially simultaneously with rotating the at least one knob, a resistance to rotation of the at least one knob is adjusted based at least partially on a compressive force exerted by the paddle against the breast (operation 308). In some examples, operation 308 further includes controlling torque resistance on the at least one knob (operation 310).

The method 300 may also include selectively engaging a solenoid actuator coupled between the at least one knob and the leadscrew (operation 312). Upon deactivation of the solenoid actuator, rotating the at least one knob (e.g., operation 304 and 306) mechanically drives linear movement of the compression device assembly along the leadscrew. In some examples, the compression device assembly is coupled to the leadscrew with a slide rail stage, and the method 300 can include determining a thickness of the compresses breast based on a position of the slide rail stage (operation 314). For example, a position sensor as described herein may perform this.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. Any number of the features of the different examples described herein may be combined into one single example and alternate examples having fewer than or more than all of the features herein described are possible. It is to be understood that terminology employed herein is used for the purpose of describing particular examples only and is not intended to be limiting. It must be noted that, as used in this specification, the singular forms "a," "an," and "the" include plural referents unless the context clearly dictates otherwise.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A compression arm device for compressing a breast in an imaging system with a compression paddle, the compression arm device comprising:
    a drive for moving the compression paddle towards the breast, the drive comprising:
        a slide rail stage configured to support the compression paddle;
        at least one knob configured to control movement of the slide rail stage;
        a clutch coupling the at least one knob to the slide rail stage; and
        an encoder coupled to the at least one knob; and
    a motor operatively coupled to the slide rail stage and configured to control movement of the slide rail stage, the motor communicatively coupled to the at least one knob, and
    wherein upon rotation of the at least one knob, the encoder communicates with the motor to drive movement of the slide rail stage, and wherein the clutch controls a torque applied on the at least one knob to provide a variable resistance to the rotation of the at least one knob during a contact of the compression paddle with the breast driven by the motor.

2. The compression arm device of claim 1, wherein the variable resistance to the rotation of the at least one knob is tactile feedback for a technician operating the at least one knob.

3. The compression arm device of claim 1, wherein the drive further comprises
    a rotatable leadscrew coupling the motor and the slide rail stage,
    wherein the slide rail stage is configured to linearly move along the leadscrew upon rotation driven by the motor, and wherein the torque applied on the at least one knob is based at least on part on a compressive force exerted by the compression paddle on the breast.

4. The compression arm device of claim 3, further comprising a brake coupled to the leadscrew, wherein the brake is selectively engageable with the leadscrew to prevent rotation of the leadscrew.

5. The compression arm device of claim 3, wherein the slide rail stage further comprises a leadscrew nut, wherein the leadscrew nut is selectively lockable to prevent rotation of the leadscrew nut.

6. The compression arm device of claim 5, wherein the slide rail stage further comprises a solenoid actuator disposed between the leadscrew nut and the at least one knob, wherein upon deactivation of the solenoid actuator, rotation of the at least one knob is configured to mechanically rotate the leadscrew nut such that the slide rail stage moves linearly along the leadscrew.

7. The compression arm device of claim 1, wherein the slide rail stage further comprises a position sensor configured to measure a linear position of the slide rail stage.

8. The compression arm device of claim 1, wherein the clutch is a magnetic particle clutch.

9. The compression arm device of claim 1, wherein the slide rail stage comprises a rotatable shaft coupled to the clutch and a transmission coupled between the rotatable shaft and the at least one knob, wherein the transmission comprises a belt and at least one gear, and wherein the at least one gear is configured to increase torque resistance applied to the at least one knob by the clutch.

10. The compression arm device of claim 1, wherein the encoder communicates velocity and position feedback of the at least one knob.

11. An imagining system comprising:
    a rotatable x-ray tube assembly; and
    a rotatable compression arm assembly comprising:
        a compression paddle;
        a receptor housing disposed opposite the compression paddle; and
        a compression arm device configured to support the compression paddle, the compression arm device comprising:
            a motor;
            a rotatable leadscrew coupled to the motor; and
            a slide rail stage coupled the leadscrew and configured to linearly move along the leadscrew, the slide rail stage comprising at least one rotatable knob positioned proximate the compression paddle,
    wherein the imaging system is selectively operable between a first condition and a second condition, and wherein in the first condition, the motor drives rotation of the leadscrew such that the slide rail stage moves relative to the receptor housing, and in the second condition, the at least one knob mechanically drives the slide rail stage along the leadscrew such that the slide rail stage moves relative to the receptor housing.

12. The imaging system of claim 11, wherein the compression paddle is laterally moveable with respect to the compression arm device.

13. The imaging system of claim 11, wherein the first condition has electrical power to the imaging system, and the second condition has at least one of (a) electrical power to the imaging system, and (b) no electrical power to the imaging system.

14. A method of compressing a breast for an imaging procedure, the method comprising:
   compressing the breast to a first condition by rotating a leadscrew with a motor so as to linearly move a paddle towards the breast, wherein the paddle is coupled to a compression device assembly linearly moveable by the rotatable leadscrew;
   compressing the breast to a second condition by rotating at least one knob of the compression device assembly so as to move the paddle further towards the breast, wherein the at least one knob includes an encoder in communication with the motor to drive rotation of the leadscrew based at least partially on rotation of the at least one knob; and
   substantially simultaneously with rotating the at least one knob, adjusting a resistance to rotation of the at least one knob based at least partially on a compressive force exerted by the paddle against the breast.

15. The method of claim 14, wherein adjusting the resistance to rotation of the at least one knob further comprises controlling torque resistance on the at least one knob.

16. The method of claim 14, wherein compressing the breast to the first condition comprises rotating the at least one knob.

17. The method of claim 14, wherein a rotational speed of the at least one knob at least partially controls a rotational speed of the leadscrew and a linear movement speed of the paddle.

18. The method of claim 14, wherein the compressive force exerted by the paddle against the breast at least partially controls a rotational speed of the leadscrew and a linear movement speed of the paddle.

19. The method of claim 14, further comprising selectively engaging a solenoid actuator coupled between the at least one knob and the leadscrew, wherein upon deactivation of the solenoid actuator, rotating the at least one knob mechanically drives linear movement of the compression device assembly along the leadscrew.

20. The method of claim 14, wherein the compression device assembly is coupled to the leadscrew with a slide rail stage, the method further comprising determining a thickness of the compresses breast based on a position of the slide rail stage.

* * * * *

UNITED STATES PATENT AND TRADEMARK OFFICE
CERTIFICATE OF CORRECTION

| | |
|---|---|
| PATENT NO. | : 11,350,891 B2 |
| APPLICATION NO. | : 16/981350 |
| DATED | : June 7, 2022 |
| INVENTOR(S) | : Kenneth Defreitas and Alan Rego |

It is certified that error appears in the above-identified patent and that said Letters Patent is hereby corrected as shown below:

In the Claims

Column 14, Line 47, please delete "11. An imagining system comprising:" and replace with -- 11. An imaging system comprising: --

Signed and Sealed this
Eighth Day of November, 2022

Katherine Kelly Vidal
*Director of the United States Patent and Trademark Office*